United States Patent
Shanley et al.

(10) Patent No.: US 7,517,362 B2
(45) Date of Patent: *Apr. 14, 2009

(54) THERAPEUTIC AGENT DELIVERY DEVICE WITH CONTROLLED THERAPEUTIC AGENT RELEASE RATES

(75) Inventors: John F. Shanley, Redwood City, CA (US); Theodore L. Parker, Danville, CA (US)

(73) Assignee: Innovational Holdings LLC., New Brunswick, NJ (US)

( * ) Notice: Subject to any disclaimer, the term of this patent is extended or adjusted under 35 U.S.C. 154(b) by 648 days.

This patent is subject to a terminal disclaimer.

(21) Appl. No.: 10/975,174

(22) Filed: Oct. 28, 2004

(65) Prior Publication Data

US 2005/0058684 A1    Mar. 17, 2005

Related U.S. Application Data

(63) Continuation of application No. 10/402,893, filed on Mar. 28, 2003, now Pat. No. 7,056,338, and a continuation-in-part of application No. 09/948,989, filed on Sep. 7, 2001, now Pat. No. 7,208,010.

(60) Provisional application No. 60/314,259, filed on Aug. 20, 2001.

(51) Int. Cl.
 *A61F 2/06* (2006.01)
(52) U.S. Cl. ............ 623/1.42; 623/1.44; 427/2.24
(58) Field of Classification Search ....... 623/1.15–1.48, 623/920; 427/2.13
See application file for complete search history.

(56) References Cited

U.S. PATENT DOCUMENTS 3,657,744 A   4/1972   Ersek
4,300,244 A   11/1981  Bokros
4,321,711 A   3/1982   Mano
4,531,936 A   7/1985   Gordon
4,542,025 A   9/1985   Tice et al.
4,580,568 A   4/1986   Gianturco
4,650,466 A   3/1987   Luther
4,733,665 A   3/1988   Palmaz
4,739,762 A   4/1988   Palmaz
4,776,337 A   10/1988  Palmaz
4,800,882 A   1/1989   Gianturco (Continued)

FOREIGN PATENT DOCUMENTS

CA    2234787    10/1998

(Continued)

OTHER PUBLICATIONS

Ran Kornowski, et al. (Washington Hospital, Wash. D.C.); "Slow-Release Taxol Coated GR11 Stents Reduce Neointima Formation in a Porcine Coronary in-Stent Rastenosis Model"; Abstract from the American Heart Association's 70th Scientific Sessions (Nov. 9-12, 1997).

(Continued)

*Primary Examiner*—Suzette J Gherbi (57) ABSTRACT

The present invention relates to implantable medical devices for the localized delivery of therapeutic agents, such as drugs, to a patient. More particularly, the invention relates to a device having a gradient of water soluble therapeutic agents within a therapeutic agent layer and a mixing layer that allows for controlled release of the therapeutic agents.

59 Claims, 1 Drawing Sheet

U.S. PATENT DOCUMENTS

| | | |
|---|---|---|
| 4,824,436 A | 4/1989 | Wolinsky |
| 4,834,755 A | 5/1989 | Silvestrini et al. |
| 4,955,878 A | 9/1990 | See et al. |
| 4,957,508 A | 9/1990 | Kaneko et al. |
| 4,960,790 A | 10/1990 | Valentino et al. |
| 4,969,458 A | 11/1990 | Wiktor |
| 4,989,601 A | 2/1991 | Marchosky |
| 4,990,155 A | 2/1991 | Wilkoff |
| 4,994,071 A | 2/1991 | MacGregor |
| 5,013,363 A | 5/1991 | Hakamatsuka et al. |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shaplan et al. |
| 5,290,271 A | 3/1994 | Jernberg |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,472,985 A | 12/1995 | Grainger et al. |
| 5,473,055 A | 12/1995 | Mongelli et al. |
| 5,500,013 A | 3/1996 | Buscemi et al. |
| 5,512,055 A | 4/1996 | Domb et al. |
| 5,516,781 A | 5/1996 | Morris et al. |
| 5,523,092 A | 6/1996 | Hanson et al. |
| 5,534,287 A | 7/1996 | Lukic |
| 5,545,208 A | 8/1996 | Wolff et al. |
| 5,545,210 A | 8/1996 | Hess et al. |
| 5,545,569 A | 8/1996 | Grainger et al. |
| 5,551,954 A | 9/1996 | Buscemi et al. |
| 5,556,413 A | 9/1996 | Lam |
| 5,563,146 A | 10/1996 | Morris et al. |
| 5,571,525 A | 11/1996 | Roorda et al. |
| 5,575,771 A | 11/1996 | Walinsky |
| 5,578,075 A | 11/1996 | Dayton |
| 5,593,434 A | 1/1997 | Williams |
| 5,595,722 A | 1/1997 | Grainger et al. |
| 5,599,844 A | 2/1997 | Grainger et al. |
| 5,605,696 A | 2/1997 | Eury et al. |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,637,113 A | 6/1997 | Tartaglia et al. |
| 5,643,314 A | 7/1997 | Carpener et al. |
| 5,646,160 A | 7/1997 | Morris et al. |
| 5,660,873 A | 8/1997 | Nikolaychik et al. |
| 5,665,591 A | 9/1997 | Sonenshein et al. |
| 5,665,728 A | 9/1997 | Morris et al. |
| 5,667,764 A | 9/1997 | Kopia et al. |
| 5,674,241 A | 10/1997 | Bley et al. |
| 5,674,278 A | 10/1997 | Boneau |
| 5,679,400 A | 10/1997 | Tuch |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,766,584 A | 6/1998 | Edelman et al. |
| 5,769,883 A | 6/1998 | Buscemi et al. |
| 5,770,609 A | 6/1998 | Grainger et al. |
| 5,773,479 A | 6/1998 | Grainger et al. |
| 5,776,181 A | 7/1998 | Lee et al. |
| 5,776,184 A | 7/1998 | Tuch |
| 5,780,807 A | 7/1998 | Saunders |
| 5,797,898 A | 8/1998 | Santini et al. |
| 5,800,507 A | 9/1998 | Schwartz |
| 5,807,404 A | 9/1998 | Richter |
| 5,811,447 A | 9/1998 | Kunz et al. |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,008 A | 11/1998 | Berg et al. |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,928,916 A | 7/1999 | Keogh |
| 5,935,506 A | 8/1999 | Schmitz et al. |
| 5,945,456 A | 8/1999 | Grainger et al. |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,972,180 A | 10/1999 | Chujo |

| | | |
|---|---|---|
| 5,976,182 A | 11/1999 | Cox |
| 5,980,551 A | 11/1999 | Summers et al. |
| 5,980,972 A | 11/1999 | Ding |
| 5,981,568 A | 11/1999 | Kunz et al. |
| 5,984,957 A | 11/1999 | Laptewicz et al. |
| 5,992,000 A | 11/1999 | Humphrey et al. |
| 5,992,769 A | 11/1999 | Wise |
| 5,994,341 A | 11/1999 | Hunter et al. |
| 5,997,703 A | 12/1999 | Richter |
| 6,007,517 A | 12/1999 | Anderson |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,074,659 A | 6/2000 | Kunz et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,099,562 A | 8/2000 | Ding et al. |
| 6,120,535 A | 9/2000 | McDonald et al. |
| 6,120,536 A | 9/2000 | Ding et al. |
| 6,120,847 A | 9/2000 | Yang et al. |
| 6,121,027 A | 9/2000 | Clapper et al. |
| 6,123,861 A | 9/2000 | Santini et al. |
| 6,131,266 A | 10/2000 | Saunders |
| 6,140,127 A | 10/2000 | Sprague |
| 6,153,252 A | 11/2000 | Hossainy et al. |
| 6,156,062 A | 12/2000 | McGuinness |
| 6,159,488 A | 12/2000 | Nagler et al. |
| 6,171,609 B1 | 1/2001 | Kunz |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,231,600 B1 | 5/2001 | Zhong |
| 6,239,118 B1 | 5/2001 | Schatz et al. |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,254,632 B1 | 7/2001 | Wu et al. |
| 6,257,706 B1 | 7/2001 | Ahn |
| 6,268,390 B1 | 7/2001 | Kunz |
| 6,273,908 B1 | 8/2001 | Ndondo-Lay |
| 6,273,910 B1 | 8/2001 | Limon |
| 6,273,913 B1 | 8/2001 | Wright et al. |
| 6,280,411 B1 | 8/2001 | Lennox |
| 6,290,673 B1 | 9/2001 | Shanley |
| 6,293,967 B1 | 9/2001 | Shanley |
| 6,299,604 B1 | 10/2001 | Ragheb et al. |
| 6,299,755 B1 | 10/2001 | Richter |
| 6,306,166 B1 | 10/2001 | Barry et al. |
| 6,306,421 B1 | 10/2001 | Kunz et al. |
| 6,309,414 B1 | 10/2001 | Rolando et al. |
| 6,312,460 B2 | 11/2001 | Drasler et al. |
| 6,331,189 B1 | 12/2001 | Wolinsky et al. |
| 6,334,807 B1 | 1/2002 | Lebel et al. |
| 6,334,871 B1 | 1/2002 | Dor et al. |
| 6,358,556 B1 | 3/2002 | Ding et al. |
| 6,358,989 B1 | 3/2002 | Kunz et al. |
| 6,369,355 B1 | 4/2002 | Saunders |
| 6,375,826 B1 | 4/2002 | Wang et al. |
| 6,378,988 B1 | 4/2002 | Taylor et al. |
| 6,379,381 B1 | 4/2002 | Hossainy et al. |
| 6,387,124 B1 | 5/2002 | Buscemi et al. |
| 6,395,326 B1 | 5/2002 | Castro et al. |
| 6,399,144 B2 | 6/2002 | Dinh et al. |
| 6,403,635 B1 | 6/2002 | Kinsella et al. |
| 6,423,092 B2 | 7/2002 | Datta et al. |
| 6,423,345 B2 | 7/2002 | Bernstein et al. |
| 6,429,232 B1 | 8/2002 | Kinsella et al. |
| 6,451,051 B2 | 9/2002 | Drasler et al. |
| 6,461,631 B1 | 10/2002 | Dunn et al. |
| 6,475,237 B2 | 11/2002 | Drasler et al. |
| 6,482,166 B1 | 11/2002 | Fariabi |
| 6,491,617 B1 | 12/2002 | Ogle et al. |
| 6,491,666 B1 | 12/2002 | Santini et al. |
| 6,491,938 B2 | 12/2002 | Kunz et al. |
| 6,497,916 B1 | 12/2002 | Taylor et al. |
| 6,500,859 B2 | 12/2002 | Kinsella et al. |
| 6,503,954 B1 | 1/2003 | Bhat et al. |
| 6,506,411 B2 | 1/2003 | Hunter et al. |
| 6,506,437 B1 | 1/2003 | Harish et al. |
| 6,515,009 B1 | 2/2003 | Kunz et al. |
| 6,528,121 B2 | 3/2003 | Ona et al. |
| 6,530,950 B1 | 3/2003 | Alvarado et al. |
| 6,537,256 B2 | 3/2003 | Santini et al. |
| 6,544,544 B2 | 4/2003 | Hunter et al. |
| 6,548,308 B2 | 4/2003 | Ellson et al. |
| 6,551,838 B2 | 4/2003 | Santini, Jr. et al. |
| 6,558,733 B1 | 5/2003 | Hossainy et al. |
| 6,562,065 B1 | 5/2003 | Shanley |
| 6,565,602 B2 | 5/2003 | Rolando et al. |
| 6,569,441 B2 | 5/2003 | Kunz et al. |
| 6,569,688 B2 | 5/2003 | Sivan et al. |
| 6,572,642 B2 | 6/2003 | Rinaldi et al. |
| 6,585,764 B2 | 7/2003 | Wright et al. |
| 6,585,765 B1 | 7/2003 | Hossainy et al. |
| 6,585,773 B1 | 7/2003 | Xie |
| 6,599,415 B1 | 7/2003 | Ku et al. |
| 6,599,928 B2 | 7/2003 | Kunz et al. |
| 6,613,084 B2 | 9/2003 | Yang |
| 6,616,765 B1 | 9/2003 | Castro et al. |
| 6,627,246 B2 * | 9/2003 | Mehta et al. ................. 427/2.1 |
| 6,635,082 B1 | 10/2003 | Hossainy et al. |
| 6,638,302 B1 | 10/2003 | Curcio et al. |
| 6,645,547 B1 | 11/2003 | Shekalim et al. |
| 6,656,162 B2 | 12/2003 | Santini et al. |
| 6,656,217 B1 | 12/2003 | Herzog et al. |
| 6,660,034 B1 | 12/2003 | Mandrusov et al. |
| 6,663,881 B2 | 12/2003 | Kunz et al. |
| 6,673,385 B1 | 1/2004 | Ding et al. |
| 6,676,987 B2 | 1/2004 | Zhong et al. |
| 6,679,980 B1 | 1/2004 | Andreacchi |
| 6,682,545 B1 | 1/2004 | Kester |
| 6,682,771 B2 | 1/2004 | Zhong et al. |
| 6,689,159 B2 | 2/2004 | Lau et al. |
| 6,689,390 B2 | 2/2004 | Bernstein et al. |
| 6,699,281 B2 | 3/2004 | Vallana et al. |
| 6,702,850 B1 * | 3/2004 | Byun et al. ................. 623/1.44 |
| 6,712,845 B2 | 3/2004 | Hossainy |
| 6,713,119 B2 | 3/2004 | Hossainy et al. |
| 6,716,444 B1 | 4/2004 | Castro et al. |
| 6,719,881 B1 | 4/2004 | Hunter et al. |
| 6,720,350 B2 | 4/2004 | Kunz et al. |
| 6,723,373 B1 | 4/2004 | Narayanan et al. |
| 6,730,064 B2 | 5/2004 | Ragheb et al. |
| 6,730,116 B1 | 5/2004 | Wolinsky et al. |
| 6,746,773 B2 | 6/2004 | Llanos et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,507 B2 | 7/2004 | Shanley et al. |
| 6,774,278 B1 | 8/2004 | Ragheb et al. |
| 6,776,796 B2 | 8/2004 | Falotico et al. |
| 6,780,424 B2 | 8/2004 | Claude |
| 6,783,543 B2 | 8/2004 | Jang |
| 6,783,793 B1 | 8/2004 | Hossainy et al. |
| 6,790,228 B2 | 9/2004 | Hossainy |
| 6,805,898 B1 | 10/2004 | Wu et al. |
| 6,808,536 B2 | 10/2004 | Wright et al. |

| Patent No. | Date | Name |
|---|---|---|
| 6,818,063 B1 | 11/2004 | Kerrigan |
| 6,846,841 B2 | 1/2005 | Hunter et al. |
| 6,849,089 B2 * | 2/2005 | Stoll .......................... 623/1.42 |
| 6,852,123 B2 | 2/2005 | Brown |
| 6,855,125 B2 | 2/2005 | Shanley |
| 6,855,770 B2 | 2/2005 | Pinchuk et al. |
| 6,860,946 B2 | 3/2005 | Hossainy et al. |
| 6,861,088 B2 | 3/2005 | Weber et al. |
| 6,863,685 B2 | 3/2005 | Davila et al. |
| 6,869,443 B2 | 3/2005 | Buscemi et al. |
| 6,887,510 B2 | 5/2005 | Villareal |
| 6,890,339 B2 | 5/2005 | Sahatjian et al. |
| 6,896,965 B1 | 5/2005 | Hossainy |
| 6,908,622 B2 | 6/2005 | Barry et al. |
| 6,908,624 B2 | 6/2005 | Hossainy et al. |
| 6,923,996 B2 | 8/2005 | Epstein et al. |
| 6,926,919 B1 | 8/2005 | Hossainy et al. |
| 6,929,660 B1 | 8/2005 | Ainsworth et al. |
| 6,939,374 B2 | 9/2005 | Banik et al. |
| 6,939,376 B2 | 9/2005 | Shulze et al. |
| 6,953,560 B1 | 10/2005 | Castro et al. |
| 6,955,723 B2 | 10/2005 | Pacetti et al. |
| 7,056,338 B2 | 6/2006 | Shanley et al. |
| 7,208,010 B2 | 4/2007 | Shanley et al. |
| 2001/0000802 A1 | 5/2001 | Soykan et al. |
| 2001/0018469 A1 | 8/2001 | Chen et al. |
| 2001/0027291 A1 | 10/2001 | Shanley |
| 2001/0027340 A1 | 10/2001 | Wright et al. |
| 2001/0029351 A1 | 10/2001 | Falotico et al. |
| 2001/0034363 A1 | 10/2001 | Li et al. |
| 2001/0044648 A1 | 11/2001 | Wolinsky et al. |
| 2001/0044652 A1 | 11/2001 | Moore |
| 2002/0002400 A1 | 1/2002 | Drasler et al. |
| 2002/0005206 A1 | 1/2002 | Falotico et al. |
| 2002/0007209 A1 * | 1/2002 | Scheerder et al. .......... 623/1.15 |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0010507 A1 | 1/2002 | Ehr et al. |
| 2002/0013619 A1 | 1/2002 | Shanley |
| 2002/0016625 A1 | 2/2002 | Falotico et al. |
| 2002/0022876 A1 | 2/2002 | Richter et al. |
| 2002/0028243 A1 | 3/2002 | Bates et al. |
| 2002/0032414 A1 | 3/2002 | Ragheb et al. |
| 2002/0038145 A1 | 3/2002 | Jang |
| 2002/0038146 A1 | 3/2002 | Harry |
| 2002/0068969 A1 | 6/2002 | Shanley et al. |
| 2002/0071902 A1 | 6/2002 | Ding et al. |
| 2002/0072511 A1 | 6/2002 | New et al. |
| 2002/0082679 A1 | 6/2002 | Sirhan et al. |
| 2002/0082680 A1 | 6/2002 | Shanley et al. |
| 2002/0082682 A1 | 6/2002 | Barclay et al. |
| 2002/0094985 A1 | 7/2002 | Herrmann |
| 2002/0107563 A1 | 8/2002 | Shanley |
| 2002/0123801 A1 | 9/2002 | Pacetti et al. |
| 2002/0127263 A1 | 9/2002 | Carlyle et al. |
| 2002/0128704 A1 | 9/2002 | Daum et al. |
| 2002/0142039 A1 | 10/2002 | Claude |
| 2002/0155212 A1 | 10/2002 | Hossainy |
| 2002/0165604 A1 | 11/2002 | Shanley |
| 2002/0193475 A1 | 12/2002 | Hossainy et al. |
| 2003/0004141 A1 | 1/2003 | Brown |
| 2003/0009214 A1 | 1/2003 | Shanley |
| 2003/0028243 A1 | 2/2003 | Bates et al. |
| 2003/0028244 A1 | 2/2003 | Bates et al. |
| 2003/0033007 A1 | 2/2003 | Sirhan et al. |
| 2003/0036794 A1 | 2/2003 | Ragheb et al. |
| 2003/0050687 A1 | 3/2003 | Schwade et al. |
| 2003/0060877 A1 | 3/2003 | Falotico et al. |
| 2003/0068355 A1 | 4/2003 | Shanley et al. |
| 2003/0077312 A1 | 4/2003 | Schmulewicz et al. |
| 2003/0083646 A1 | 5/2003 | Sirhan et al. |
| 2003/0086957 A1 | 5/2003 | Hughes et al. |
| 2003/0088307 A1 | 5/2003 | Shulze et al. |
| 2003/0100865 A1 | 5/2003 | Santini et al. |
| 2003/0105511 A1 | 6/2003 | Welsh et al. |
| 2003/0125800 A1 | 7/2003 | Shulze et al. |
| 2003/0125803 A1 | 7/2003 | Vallana et al. |
| 2003/0157241 A1 | 8/2003 | Hossainy et al. |
| 2003/0167085 A1 | 9/2003 | Shanley |
| 2003/0176915 A1 | 9/2003 | Wright et al. |
| 2003/0181973 A1 | 9/2003 | Sahota |
| 2003/0199970 A1 | 10/2003 | Shanley |
| 2003/0204239 A1 | 10/2003 | Carlyle et al. |
| 2003/0216699 A1 | 11/2003 | Falotico |
| 2003/0225420 A1 | 12/2003 | Wardle |
| 2004/0006382 A1 | 1/2004 | Sohier |
| 2004/0024449 A1 | 2/2004 | Boyle |
| 2004/0073296 A1 | 4/2004 | Epstein et al. |
| 2004/0098117 A1 | 5/2004 | Hossainy et al. |
| 2004/0122505 A1 | 6/2004 | Shanley |
| 2004/0122506 A1 | 6/2004 | Shanley et al. |
| 2004/0127976 A1 * | 7/2004 | Diaz .......................... 623/1.42 |
| 2004/0127977 A1 | 7/2004 | Shanley |
| 2004/0142014 A1 | 7/2004 | Litvack et al. |
| 2004/0143321 A1 | 7/2004 | Litvack et al. |
| 2004/0143322 A1 | 7/2004 | Litvack et al. |
| 2004/0166140 A1 | 8/2004 | Santini et al. |
| 2004/0193255 A1 | 9/2004 | Shanley et al. |
| 2004/0202692 A1 | 10/2004 | Shanley et al. |
| 2004/0204756 A1 | 10/2004 | Diaz et al. |
| 2004/0208985 A1 | 10/2004 | Rowan et al. |
| 2004/0220660 A1 | 11/2004 | Shanley et al. |
| 2004/0220665 A1 | 11/2004 | Hossainy et al. |
| 2004/0225350 A1 | 11/2004 | Shanley |
| 2004/0234737 A1 | 11/2004 | Pacetti |
| 2004/0249449 A1 | 12/2004 | Shanley et al. |
| 2005/0038505 A1 | 2/2005 | Shulze et al. |
| 2005/0049693 A1 | 3/2005 | Walker |
| 2005/0055078 A1 | 3/2005 | Campbell |
| 2005/0058684 A1 | 3/2005 | Shanley et al. |
| 2005/0059991 A1 | 3/2005 | Shanley |
| 2005/0060020 A1 | 3/2005 | Jenson |
| 2005/0064088 A1 | 3/2005 | Fredrickson |
| 2005/0074545 A1 | 4/2005 | Thoman |
| 2005/0075714 A1 | 4/2005 | Cheng et al. |
| 2005/0079199 A1 | 4/2005 | Heruth et al. |
| 2005/0084515 A1 | 4/2005 | Udipi et al. |
| 2005/0100577 A1 | 5/2005 | Parker et al. |
| 2005/0106210 A1 | 5/2005 | Ding et al. |
| 2005/0113903 A1 | 5/2005 | Rosenthal et al. |
| 2005/0119720 A1 | 6/2005 | Gale et al. |
| 2005/0158360 A1 | 7/2005 | Falotico et al. |
| 2005/0169969 A1 | 8/2005 | Li et al. |
| 2005/0177226 A1 | 8/2005 | Banik et al. |
| 2005/0187611 A1 | 8/2005 | Ding et al. |
| 2005/0197691 A1 | 9/2005 | Hezi-Yamit et al. |
| 2005/0208200 A1 | 9/2005 | Ding et al. |
| 2005/0222676 A1 | 10/2005 | Shanley et al. |
| 2005/0233062 A1 | 10/2005 | Hossainy et al. |
| 2005/0234538 A1 | 10/2005 | Litvack et al. |
| 2005/0234544 A1 | 10/2005 | Shanley |
| 2005/0251248 A1 | 11/2005 | Chandresekara et al. |
| 2005/0256564 A1 | 11/2005 | Yang et al. |
| 2005/0261762 A1 | 11/2005 | Hezi-Yamit |
| 2005/0271697 A1 | 12/2005 | Litvack |
| 2005/0273161 A1 | 12/2005 | Malik et al. |
| 2005/0278016 A1 | 12/2005 | Welsh et al. |
| 2006/0008503 A1 | 1/2006 | Shanley |
| 2006/0009838 A1 | 1/2006 | Shanley et al. |
| 2006/0030931 A1 | 2/2006 | Shanley |
| 2006/0035879 A1 | 2/2006 | Prescott |
| 2006/0064157 A1 | 3/2006 | Shanley |
| 2006/0096660 A1 | 5/2006 | Diaz et al. |
| 2006/0122688 A1 | 6/2006 | Shanley et al. |

| | | | |
|---|---|---|---|
| 2006/0122697 A1 | 6/2006 | Shanley et al. | |
| 2006/0177564 A1 | 8/2006 | Diaz et al. | |
| 2006/0178734 A1 | 8/2006 | Parker et al. | |
| 2006/0178735 A1 | 8/2006 | Litvack et al. | |

FOREIGN PATENT DOCUMENTS

| | | |
|---|---|---|
| CA | 2234787 B1 | 10/1998 |
| DE | 20200220 | 3/2002 |
| EP | 294905 | 12/1988 |
| EP | 294905 B1 | 12/1988 |
| EP | 335341 B1 | 10/1989 |
| EP | 375520 B1 | 6/1990 |
| EP | 470246 | 2/1992 |
| EP | 470569 B1 | 2/1992 |
| EP | 540290 B2 | 5/1993 |
| EP | 543653 | 5/1993 |
| EP | 551182 | 7/1993 |
| EP | 566245 | 10/1993 |
| EP | 567816 A1 | 11/1993 |
| EP | 568310 | 11/1993 |
| EP | 604022 | 6/1994 |
| EP | 623354 | 11/1994 |
| EP | 627226 | 12/1994 |
| EP | 679373 | 11/1995 |
| EP | 706376 | 4/1996 |
| EP | 716836 | 6/1996 |
| EP | 734698 B1 | 10/1996 |
| EP | 734699 B1 | 10/1996 |
| EP | 747069 | 12/1996 |
| EP | 752885 | 1/1997 |
| EP | 770401 B1 | 5/1997 |
| EP | 797963 | 10/1997 |
| EP | 807424 B2 | 11/1997 |
| EP | 809515 | 12/1997 |
| EP | 832655 | 4/1998 |
| EP | 875218 | 4/1998 |
| EP | 850651 | 7/1998 |
| EP | 897700 B1 | 2/1999 |
| EP | 950386 | 10/1999 |
| EP | 959812 | 12/1999 |
| EP | 968013 | 1/2000 |
| EP | 975340 | 2/2000 |
| EP | 980280 | 2/2000 |
| EP | 1118325 | 7/2001 |
| EP | 1132058 | 9/2001 |
| EP | 1155690 | 11/2001 |
| EP | 1172074 | 1/2002 |
| EP | 1181903 | 2/2002 |
| EP | 1181943 | 2/2002 |
| EP | 1222941 | 7/2002 |
| EP | 1223305 A2 | 7/2002 |
| EP | 1236478 | 9/2002 |
| EP | 1277449 | 1/2003 |
| EP | 711158 | 3/2003 |
| EP | 1330993 | 7/2003 |
| EP | 1341479 | 9/2003 |
| EP | 1470828 | 10/2004 |
| EP | 1472992 | 11/2004 |
| EP | 1479401 | 11/2004 |
| EP | 1493456 | 1/2005 |
| EP | 1493457 | 1/2005 |
| EP | 1498084 | 1/2005 |
| EP | 1500406 | 1/2005 |
| EP | 1500407 | 1/2005 |
| EP | 1504775 | 2/2005 |
| EP | 1518570 | 3/2005 |
| EP | 1527754 | 5/2005 |
| EP | 1557183 | 7/2005 |
| EP | 1559439 | 8/2005 |
| EP | 1561436 | 8/2005 |
| EP | 1566187 | 8/2005 |
| EP | 1570871 | 9/2005 |
| EP | 1574228 | 9/2005 |
| EP | 1582180 | 10/2005 |
| EP | 1582225 | 10/2005 |
| EP | 1586338 | 10/2005 |
| EP | 1588725 | 10/2005 |
| EP | 1588726 | 10/2005 |
| EP | 1588727 | 10/2005 |
| EP | 1600123 | 11/2005 |
| EP | 1600180 | 11/2005 |
| FR | 2764794 A1 | 12/1998 |
| WO | WO-9001969 | 3/1990 |
| WO | WO-9013332 | 11/1990 |
| WO | 1991010424 A2 | 7/1991 |
| WO | 1991011193 A1 | 8/1991 |
| WO | 1991012779 A1 | 9/1991 |
| WO | WO-9112779 | 11/1991 |
| WO | WO-9200747 | 1/1992 |
| WO | WO-200589951 | 2/1992 |
| WO | WO-200592242 | 3/1992 |
| WO | 1992015286 A1 | 9/1992 |
| WO | 1992012717 A2 | 10/1992 |
| WO | WO-9306792 | 4/1993 |
| WO | WO-9311120 | 6/1993 |
| WO | WO-9407529 | 4/1994 |
| WO | WO-9413268 | 6/1994 |
| WO | WO-9416706 | 8/1994 |
| WO | WO-9421308 | 9/1994 |
| WO | WO-9424961 | 11/1994 |
| WO | WO-9424962 | 11/1994 |
| WO | WO-9503036 | 2/1995 |
| WO | WO-9503795 | 2/1995 |
| WO | WO-9524908 | 9/1995 |
| WO | 1996003092 A1 | 2/1996 |
| WO | WO-9625176 | 8/1996 |
| WO | 1996029028 A1 | 9/1996 |
| WO | 1996032907 A1 | 10/1996 |
| WO | WO-9632907 | 10/1996 |
| WO | 1997004721 A1 | 2/1997 |
| WO | WO-9710011 | 3/1997 |
| WO | 1998008566 A1 | 3/1998 |
| WO | 1998018407 A1 | 5/1998 |
| WO | 1998019628 A1 | 5/1998 |
| WO | 1998058600 A1 | 5/1998 |
| WO | WO-9823228 | 6/1998 |
| WO | WO-9823244 | 6/1998 |
| WO | WO-9836784 | 8/1998 |
| WO | 1999015108 A1 | 4/1999 |
| WO | WO-9916386 | 4/1999 |
| WO | WO-9916477 | 4/1999 |
| WO | WO-9923977 | 5/1999 |
| WO | 1999044536 A1 | 9/1999 |
| WO | 1999049928 A1 | 10/1999 |
| WO | WO-9949928 | 10/1999 |
| WO | WO-9955396 | 11/1999 |
| WO | 2000010613 A2 | 3/2000 |
| WO | WO-0010622 | 3/2000 |
| WO | WO-0045744 | 8/2000 |
| WO | 2000069368 A2 | 11/2000 |
| WO | WO-0071054 | 11/2000 |
| WO | WO-0110421 | 2/2001 |
| WO | WO-0117577 | 3/2001 |
| WO | 2001045862 A1 | 6/2001 |
| WO | WO-0145763 | 6/2001 |
| WO | WO-0149338 | 7/2001 |
| WO | WO-0152915 | 7/2001 |
| WO | WO-0187376 | 11/2001 |
| WO | WO-0217880 | 3/2002 |
| WO | WO-0226162 | 4/2002 |
| WO | WO-0226281 | 4/2002 |
| WO | WO-0232347 | 4/2002 |
| WO | WO-0241931 A2 | 5/2002 |
| WO | WO-0241931 A3 | 5/2002 |
| WO | WO-0243788 | 6/2002 |

| | | |
|---|---|---|
| WO | WO-02060506 | 8/2002 |
| WO | WO-02087586 | 11/2002 |
| WO | WO-03015664 | 2/2003 |
| WO | WO-03018083 | 3/2003 |
| WO | WO-03035132 | 5/2003 |
| WO | WO-03077730 | 9/2003 |
| WO | WO-03082364 | 10/2003 |
| WO | WO-03082368 | 10/2003 |
| WO | WO-2004000379 | 12/2003 |
| WO | WO-2004043510 | 5/2004 |
| WO | WO-2004043511 | 5/2004 |
| WO | WO-2004045578 | 6/2004 |
| WO | WO-2004087015 | 10/2004 |
| WO | WO-2004091714 | 10/2004 |
| WO | WO-2004096176 | 11/2004 |
| WO | WO-2004096311 | 11/2004 |
| WO | WO-2004098451 | 11/2004 |
| WO | WO-2004098671 | 11/2004 |
| WO | WO-2004101018 | 11/2004 |
| WO | WO-2004103428 | 12/2004 |
| WO | WO-2005000939 | 1/2005 |
| WO | WO-2005004945 | 1/2005 |
| WO | WO-2005004946 | 1/2005 |
| WO | WO-2005007035 | 1/2005 |
| WO | WO-2005011766 | 2/2005 |
| WO | WO-2005011767 | 2/2005 |
| WO | WO-2005011769 | 2/2005 |
| WO | WO-2005011770 | 2/2005 |
| WO | WO-2005016187 | 2/2005 |
| WO | WO-2005016396 | 2/2005 |
| WO | WO-2005018606 | 3/2005 |
| WO | WO-2005027794 | 3/2005 |
| WO | WO-2005034805 | 4/2005 |
| WO | WO-2005034806 | 4/2005 |
| WO | WO-2005037444 | 4/2005 |
| WO | WO-2005037447 | 4/2005 |
| WO | WO-2005040416 | 5/2005 |
| WO | WO-2005044506 | 5/2005 |
| WO | WO-2005046521 | 5/2005 |
| WO | WO-2005049678 | 6/2005 |
| WO | WO-2005051449 | 6/2005 |
| WO | WO-2005053571 | 6/2005 |
| WO | WO-2005053937 | 6/2005 |
| WO | WO-2005082283 | 9/2005 |
| WO | WO-2005089824 | 9/2005 |
| WO | WO-2005089825 | 9/2005 |
| WO | WO-2005092406 | 10/2005 |
| WO | WO-2005094930 | 10/2005 |
| WO | WO-2005097066 | 10/2005 |
| WO | WO-2005097220 | 10/2005 |
| WO | WO-2005112570 | 12/2005 |
| WO | WO-2005115277 | 12/2005 |
| WO | WO-2005120397 | 12/2005 |
| WO | WO-2006007473 | 1/2006 |
| WO | WO-2006012034 | 2/2006 |
| WO | WO-2006012060 | 2/2006 |
| WO | WO-2006036319 | 4/2006 |

OTHER PUBLICATIONS

David A. Cox, MD, et al.; "Effect of Local Delivery of Heparin and Methotrexate on Neointimal Proliferation in Stented Porcine Coronary Arteries"; Coronary Artery Disease, Mar. 1992, vol. 3, No. 3: 237-248; University of AL, USA.

Tom Lambert, et al.; "A New Method for Arterial Drug Delivery Via Removable Stent"; JACC vol. 21, No. 2, Feb. 1993, abstract 834-2; American College of Cardiology, Bethesda, MD, USA.

DAV: Circulation, 1993, 89 (2/2): 834-2.

Bonnie L. Hiatt, et al. "The Drug-Eluting Stent: Is It the Holy Grail?" Reviews in Cardiovascular Medicine. (2001) vol. 2, No. 4, pp. 190-196P032-C1.

Patrick W. Serruys, et al., "Heparin-Coated Palmaz-Schatz Stents in Human Coronary Arteries" Circulation, 1996; 93:412-422.

Jennifer L. West, "Drug Delivery—Pulsed Polymers." Nature Materials, vol. 2, Nov. 2003, pp. 709-710.

Ruaraidh A. Hill, et al. "Drug-eluting Stents: an Early Systematic Review to Inform Policy." European Heart Journal (2004) 25, 902-919.

William L. Hunter, et al., Local Delivery of Chemotherapy: A Supplement to Existing Cancer Treatments A Case for Surgical Pastes and Coated Stents, Elseriver Science, 069-409X/1997.

P.W. Serruys, et al., The Effect of Variale Dose and Release Kinetics on Neointimal Hyperplasia Using a Novel Paclitaxel-Eluting Stent Platform, Journal of the American College of Cardiology, vol. 46, No. 2, 2005.

Steven R. Bailey, et al., Coating of Endovascular Stents, Textbook of Interventional Cardiology, 1994.

Dorin Panescu, "Drug Eluting Stents," IEEE Engineering in Medicine and Biology Magazine, Mar./Apr. 2004.

Georgina M. Nemecek, et al., "Terbinafine Inhibits the Mitogenic Response to Platelet-Derived Growth Factor in Vitro and Neointimal Proliferation in Vivo," The Journal of Pharmacology and Experimental Therapeutics, vol. 248, No. 3.

J. Eduardo Sousa, et al., New Frontiers in Cardiology Drug-Eluting Stents: Part I, Circulation, 2003; 107:2274-2279.

Manfred Boehm, et al., "Cell Cycle and Cell Migration: New Pieces to the Puzzle," Circulation 2001;103:2879-2881.

Ruediger C. Braun-Dullaeus, et al., "Cell Cycle Progression: New Therapeutic Target for Vascular Proliferative Disease," Circulation. 1998;98:82-89.

Eric J. Topol, et al., "Frontiers in Interventional Cardiology," Circulation. 1998;98:1802-1820.

Babapulle, et al., Coated Stents for the Prevention of Restenosis: Part II, Circulation, Nov. 26, 2002.

Stone, et al., One Year Clinical Results with the Slow-Release, Polymer-Based, Padlitaxel-Eluting TAXUS Stent, Circulation, Apr. 27, 2004.

Moussa, et al., Impact of Sirolimus-Eluting Stents on Outcome in Diabetic Patients, Circulation, May 18, 2004.

Sriram, et al., Cell Cycle in Vasculoproliferative Diseases, May 15, 2001.

Kereiakes, et al., Hipporates Revisited, The Evidence for Drug-Eluting Stents, Circulation, Jun. 24, 2003.

Suzuki, et al., Stent-Based Delivery of Sirolimus Reduces Neointimal Formation in a Porcine Cornonary Model,Circulation, Sep. 4, 2001.

Morice, et al., The Ravel Trial, Evidence-Based Medecine.

Hwang,C.W. et. al. "Physiological Transport Forces Govern Drug Distribution for Stent Based Delivery". Circulation, Aug. 17, 2001, pp. 1-8.

Emanelsson, H., et al., The Jostent Coronary Stent Range, Chapter 19.

* cited by examiner

THERAPEUTIC AGENT DELIVERY DEVICE WITH CONTROLLED THERAPEUTIC AGENT RELEASE RATES

This application is a continuation of, and claims priority under 35 U.S.C. § 120 to, U.S. application Ser. No. 10/402,893, filed Mar. 28, 2003 now U.S. Pat. No. 7,056,338. This application is also a continuation-in-part of, and claims priority under 35 U.S.C. § 120 to, U.S. application Ser. No. 09/948,989, filed Sep. 7, 2001, now U.S. Pat. No. 7,208,010, which claims priority under 35 U.S.C. § 119 to U.S. Provisional Application No. 60/314,259, filed Aug. 20, 2001.

FIELD OF THE INVENTION

The invention relates to a therapeutic agent delivery device which comprises a gradient of therapeutic agent within mixing layers which provides for the controlled release of water soluble therapeutic agents.

DESCRIPTION OF THE RELATED ART

Implantable medical devices are often used for delivery of a beneficial agent, such as a drug, to an organ or tissue in the body at a controlled delivery rate over an extended period of time. These devices may deliver agents to a wide variety of bodily systems to provide a wide variety of treatments.

One of the many implantable medical devices which have been used for local delivery of beneficial agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as stainless steel, gold, silver, tantalum, titanium, and shape memory alloys, such as Nitinol.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. Despite the introduction of improved surgical techniques, devices, and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

One of the techniques under development to address the problem of restenosis is the use of surface coatings of various beneficial agents on stents. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stent surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall. This is undesirable for a number of reasons, including increased trauma to the vessel wall during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, duration of drug delivery, and the like that can be achieved.

In addition to sub-optimal release profiles, there are further problems with surface coated stents. The fixed matrix polymer carriers frequently used in the device coatings typically retain approximately 30% of the beneficial agent in the coating indefinitely. Since these beneficial agents are frequently highly cytotoxic, sub-acute and chronic problems such as chronic inflammation, late thrombosis, and late or incomplete healing of the vessel wall may occur. Additionally, the carrier polymers themselves are often highly inflammatory to the tissue of the vessel wall. On the other hand, use of biodegradable polymer carriers on stent surfaces can result in the creation of "virtual spaces" or voids between the stent and tissue of the vessel wall after the polymer carrier has degraded, which permits differential motion between the stent and adjacent tissue. Resulting problems include micro-abrasion and inflammation, stent drift, and failure to re-endothelialize the vessel wall.

Another significant problem is that expansion of the stent may stress the overlying polymeric coating causing the coating to plastically deform or even to rupture, which may therefore effect drug release kinetics or have other untoward effects. Further, expansion of such a coated stent in an atherosclerotic blood vessel will place circumferential shear forces on the polymeric coating, which may cause the coating to separate from the underlying stent surface. Such separation may again have untoward effects including embolization of coating fragments causing vascular obstruction.

In addition, it is not currently possible to deliver some drugs with a surface coating for a variety of reasons. In some cases, the drugs are sensitive to water, other compounds, or conditions in the body which degrade the drugs. For example, some drugs lose substantially all their activity when exposed to water for a period of time. When the desired treatment time is substantially longer than the half life of the drug in water the drug cannot be delivered by know coatings. Other drugs, such as protein or peptide based therapeutic agents, lose activity when exposed to enzymes, pH changes, or other environmental conditions. And finally drugs that are highly-soluble in water tend to be released from the coatings at an undesirably high rate and do not remain localized for a therapeutically useful amount of time. These types of drugs which are sensitive to compounds or conditions in the body often cannot be delivered using surface coatings.

Accordingly, it would be desirable to provide a beneficial agent delivery device for delivery of agents, such as drugs, to a patient while protecting the agent from compounds or conditions in the body which would degrade the agent.

SUMMARY OF THE INVENTION

The present invention relates to medical device for the controlled delivery of therapeutic agents where the release of the therapeutic agent is mediated by a mixing layer.

In one of its device aspects the present invention provides for an implantable medical device comprising an implantable device body having a plurality of holes; a therapeutic agent provided in a first therapeutic agent layer and contained within the plurality of holes in the device body; and at least one mixing layer provided adjacent the first therapeutic agent layer in the plurality of holes; wherein the therapeutic agent layer and the at least one mixing layer together contain a concentration gradient of said therapeutic agent and allow for the controlled release of the therapeutic agent contained within the therapeutic agent layer and the at least one mixing layer.

In another of its device aspects the present invention provides for an implantable medical device comprising an implantable device body having a plurality of holes; a therapeutic agent within the plurality of holes in the device body provided in a therapeutic agent layer; and a mixing layer provided in the plurality of holes; wherein the therapeutic agent layer and the mixing layer contain a concentration gradient of said therapeutic agent created by delivering a mixing layer material without the therapeutic agent and liquefying a portion of the therapeutic agent layer with the mixing layer material, whereby the mixing layer has a lesser amount of therapeutic agent contained therein than the therapeutic agent layer.

In yet another of its device aspects, the present invention provides for an implantable medical device comprising an implantable device body having a plurality of through holes, a plurality of layers of a bioresorbable polymer formed in the through holes to form a barrier layer at a first side of the holes, a plurality of layers of a bioresorbable polymer and drug formed in the through holes to form a drug layer adjacent the barrier layer, a plurality of layers of a bioresorbable polymer formed in the through holes to form a cap layer at a second side of the holes, and wherein the drug layer and the cap layer mix to form a concentration gradient.

The mixing layers are preferably a pharmaceutically acceptable bioresorbable matrix, more preferably pharmaceutically acceptable polymers. Even more preferably the mixing layers are selected from the group consisting of polylactic acid, polyglycolic acid, polylactic-co-glycolic acid, polylactic acid-co-caprolactone, polyethylene glycol, polyethylene oxide, poly lactic acid-block-poly ethylene glycol, poly glycolic acid-block-poly ethylene glycol, poly lactide-co-glycolide-block-poly ethylene glycol, poly ethylene glycol-block-lipid, polyvinyl pyrrolidone, poly vinyl alcohol, a glycosaminoglycan, polyorthoesters, polysaccharides, polysaccharide derivatives, polyhyaluronic acid, polyalginic acid, chitin, chitosan, chitosan derivatives, cellulose, hydroxyethylcellulose, hydroxypropylcellulose, carboxymethylcellulose, polypeptides, polylysine, polyglutamic acid, albumin, polyanhydrides, polyhydroxy alkonoates, polyhydroxy valerate, polyhydroxy butyrate, proteins, polyphosphate esters, lipids, and mixtures thereof.

The therapeutic agent layer preferably comprises the therapeutic agent and a water soluble binding agent. The water soluble binding agent is preferably selected from poly ethylene glycol, poly ethylene oxide, poly vinylpyrrolidone, poly vinyl alcohol, a glycosaminoglycan, polysaccharides, polysaccharide derivatives, poly hyaluronic acid, poly alginic acid, chitin, chitosan, chitosan derivatives, cellulose, hydroxyethyl cellulose, hydroxypropyl cellulose, carboxymethyl cellulose, poly peptides, poly lysine, poly glutamic acid, and proteins, such as albumin.

The liquefied therapeutic agent layer comprises from about 20% to about 95% therapeutic agent and from about 5% to about 70% pharmaceutically acceptable polymer preferably from about 50% to about 95% therapeutic agent and from about 5% to about 50% pharmaceutically acceptable polymer, more preferably from about 50% to about 60% therapeutic agent and from about 40% to about 50% pharmaceutically acceptable polymer.

The therapeutic agent is preferably antithrombotic agents, a antineoplastic agent, a neoplastic agent, an antiproliferative agent, an antisense compound, an immunosuppresant, an angiogenic agent, an angiogenic factor, an antiangiogenic agent, or an anti-inflammatory agent, or combinations thereof. More preferably the therapeutic agent is of 2-chloro-deoxyadenosine, bivalirudin, Resten NG, or an oliogonucleotide, or mixtures thereof.

The therapeutic agent maybe homogeneously or heterogeneously dispersed in the therapeutic agent layer and/or the mixing layer(s). The therapeutic agent may be homogeneously or heterogeneously disposed in a layer as a solid particle dispersion, encapsulated agent dispersion, an emulsion, a suspension, a liposome, niosome, or a microparticle, wherein said niosome, liposome or microparticle comprise a homogeneous or heterogeneous mixture of the therapeutic agent. When a therapeutic agent is homogeneously disposed in a therapeutic agent layer, it may be a solid-solution or a multi-phase mixture.

Optionally the liquefied bioresorbable polymer loaded into the holes does not contain the therapeutic agent.

The implantable medical device is useful in the treatment of restenosis and inflammation and is preferably a stent.

The bioresorbable polymers, binding agents of the individual layers may be the same or different. In one embodiment, the polymers used in the therapeutic agent layer is different than the polymer used in the mixing layer. The polymers and binging agents of the individual layers maybe liquified by dissolution of the materials in a solvent or by maintaining the materials at a temperature that is higher than their melting points, or glass transition temperatures.

The implantable medical device may optionally further comprise a barrier layer, wherein the barrier layer is located adjacent the therapeutic agent layer. The barrier layer is formed by loading into the plurality of holes an amount of a liquified biocompatible polymer, which amount is sufficient to form a barrier layer, wherein the barrier layer is located adjacent the therapeutic agent layer.

In one of its method aspects the present invention provides for an method for preparing an implantable medical device as described herein above, which method comprises:

a) providing an implantable medical device with a plurality of holes;

b) loading into the plurality of holes an amount of a liquified therapeutic agent, which amount is sufficient to form a therapeutic agent layer;

c) allowing said liquified therapeutic agent layer to at least partially solidify;

d) loading into the plurality of holes an amount of a liquified bioresorbable polymer which amount is sufficient to liquify a portion of the therapeutic agent layer, thereby allowing a portion of the therapeutic agent layer to be disposed within a mixing layer;

e) allowing said liquified bioresorbable polymer and said portion of the therapeutic agent layer to solidify;

wherein an amount of therapeutic agent contained within the mixing layer upon solidification is smaller than an amount of therapeutic agent contained in the therapeutic agent layer and further wherein steps d and e may optionally be repeated to form multiple mixing layers.

BRIEF DESCRIPTION OF THE DRAWING FIGURES

The invention will now be described in greater detail with reference to the preferred embodiments illustrated in the accompanying drawings, in which like elements bear like reference numerals, and wherein.

DETAILED DESCRIPTION OF THE INVENTION

The present invention relates to a delivery device for delivery of water soluble therapeutic agents to a patient. More particularly, the invention relates to a medical device having therapeutic agents protected from premature release into a patient by one or more mixing layers. Details for the device design, therapeutic agents, therapeutic agent layers, and mixing layers may also be found in U.S. patent application Ser. No. 10/253,020, filed on Sep. 23, 2002, incorporated herein by reference in its entirety. First, the following terms, as used herein, shall have the following meanings:

The term "beneficial agent" as used herein is intended to have its broadest possible interpretation and is used to include any therapeutic agent or drug, as well as inactive agents such as barrier layers, carrier layers, therapeutic layers or mixing layers.

The terms "drug" and "therapeutic agent" are used interchangeably to refer to any therapeutically active substance that is delivered to a bodily conduit of a living being to produce a desired, usually beneficial, effect. The present invention is particularly well suited for the delivery of antineoplastic, angiogenic factors, immuno-suppressants, and antiproliferatives (anti-restenosis agents) such as paclitaxel, Rapamycin or 2-chlorodeoxyadenosine, for example, and antithrombins such as heparin, for example.

The therapeutic agents used in the present invention include classical low molecular weight therapeutic agents commonly referred to as drugs including all classes of action as exemplified by, but not limited to: antineoplastic, immunosuppressants, antiproliferatives, antithrombins, antiplatelet, antilipid, anti-inflammatory, angiogenic, anti-angiogenic, vitamins, ACE inhibitors, vasoactive substances, antimitotics, metello-proteinase inhibitors, NO donors, estradiols, anti-sclerosing agents, alone or in combination. Therapeutic agent also includes higher molecular weight substances with drug like effects on target tissue sometimes called biologic agents including but not limited to: peptides, lipids, protein drugs, protein conjugates drugs, enzymes, oligonucleotides, ribozymes, genetic material, prions, virus, bacteria, and eucaryotic cells such as endothelial cells, monocyte/macrophages or vascular smooth muscle cells to name but a few examples. The therapeutic agent may also be a pro-drug, which metabolizes into the desired drug when administered to a host. In addition, the therapeutic agents may be preformulated as a microcapsules, microspheres, microbubbles, liposomes, niosomes, emulsions, dispersions or the like before it is incorporated into the therapeutic layer. The therapeutic agent may also be radioactive isotopes or agents activated by some other form of energy such as light or ultrasonic energy, or by other circulating molecules that can be systemically administered.

A water soluble drug is one that has a solubility of greater than 1.0 mg/mL in water at body temperature.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, and/or modulate the release of the therapeutic agent into the body. A matrix is also a medium that may simply provide support, structural integrity or structural barriers. The matrix may be polymeric, non-polymeric, hydrophobic, hydrophilic, lipophilic, amphiphilic, and the like.

The term "bioresorbable" refers to a matrix, as defined herein, that can be broken down by either chemical or physical process, upon interaction with a physiological environment. The matrix can erode or dissolve. A bioresorbable matrix serves a temporary function in the body, such as drug delivery, and is then degraded or broken into components that are metabolizable or excretable, over a period of time from minutes to years, preferably less than one year, while maintaining any requisite structural integrity in that same time period.

The term "pharmaceutically acceptable" refers to a matrix or an additive, as defined herein, that is not toxic to the host or patient. When in reference to a matrix, it provides the appropriate storage and/or delivery of therapeutic, activating or deactivating agents, as defined herein, and does not interfere with the effectiveness or the biological activity of the agent.

The term "mixing layer" refers to a matrix layer which is adjacent a therapeutic agent layer. Before the mixing layer is introduced to the device, the mixing layer preferably contains no therapeutic agent, or it contains a therapeutic agent which is different from the therapeutic agent of the therapeutic agent layer. The mixing layer is introduced in a liquified state and may mix with the therapeutic agent layer causing the mixing layer to incorporate a portion of the adjacent therapeutic agent layer once the layer has at least partially solidified. The mixing layer may also serve to control the rate at which a drug is released into the reaction environment. The release rate can be controlled by the rate of erosion or dissolution of the mixing layer or by the rate of diffusion of the therapeutic agent from within the mixing and therapeutic agent layers. The mixing layer is preferably bioresorbable.

The term "erosion" refers to the process by which the components of a medium or matrix are bioresorbed and/or degraded and/or broken down by either chemical or physical processes. For example in reference to polymers, erosion can occur by cleavage or hydrolysis of the polymer chains, such that the molecular weight of the polymer is lowered. The polymer of lower molecular weight will have greater solubility in water and is therefore dissolved away. In another example, erosion occurs by physically breaking apart upon interaction with a physiological environment.

The term "erosion rate" is a measure of the amount of time it takes for the erosion process to occur and is usually report in unit area per unit time.

The term "degrade" or "deactivate" refers to any process that causes an active component, such as a therapeutic agent, to become unable, or less able, to perform the action which it was intended to perform when incorporated in the device.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000. Examples of polymers include but are not limited to, poly-α-hydroxy acid esters such as, polylactic acid, polyglycolic acid, polylactic-co-glycolic acid, polylactic acid-co-caprolactone; polyethylene glycol and polyethylene oxide, polyvinyl pyrrolidone, polyorthoesters; polysaccharides and polysaccharide derivatives such as polyhyaluronic acid, polyalginic acid, chitin, chitosan, chitosan derivatives, cellulose, hydroxyethylcellulose, hydroxypropylcellulose, carboxymethylcellulose; polypeptides, and proteins such as polylysine, polyglutamic acid, albumin; polyanhydrides; polyhydroxy alkonoates such as polyhydroxy valerate, polyhydroxy butyrate, and the like.

The term "lipid", as used herein, refers to a matrix that comprises preferably non-polymeric small organic, synthetic or naturally-occurring, compounds which are generally amphipathic and biocompatible. The lipids typically comprise a hydrophilic component and a hydrophobic component. Exemplary lipids include, for example, fatty acids, fatty acid esters, neutral fats, phospholipids, glycolipids, aliphatic alcohols, waxes, terpenes, steroids and surfactants. Term lipid is also meant to include derivatives of lipids. More specifically the term lipids includes but is not limited to phosphatidylcholine, phosphatidylethanolamine, phosphatidylserine, sphingomyelin as well as synthetic phospholipids such as dimyristoyl phosphatidylcholine, dipalmitoyl phosphatidylcholine, distearoyl phosphatidylcholine, distearoyl phosphatidylglycerol, dipalmitoyl phosphatidyl-glycerol, dimyristoyl phosphatidylserine, distearoyl phosphatidylserine and dipalmitoyl phosphatidylserine.

The term "additives" refers to pharmaceutically acceptable compounds, materials, and compositions that may be included in a matrix along with a therapeutic agent. An additive may be encapsulated in or on or around a matrix. It may be homogeneously or heterogeneously disposed, as defined herein, in the matrix. Some examples of additives are pharmaceutically acceptable excipients, adjuvants, carriers, antioxidants, preservatives, buffers, antacids, and the like, such as those disclosed in Remington: The Science and Practice of Pharmacy, Gennaro, ed., Mack Publishing Co., Easton, Pa., 19th ed., 1995.

The term "holes" refers to holes of any shape and includes both through-openings and recesses.

The term "reaction environment" or "environment" refers to the area between a tissue surface abutting the device and the first intact layer of beneficial agent within a hole in the medical device.

The term "liquified" is used herein to define a component which is put in a liquid state either by heating the component to a temperature higher than its melting point, or glass transition temperature, or by dissolving the component in a solvent. The typical liquified materials of the present invention will have a viscosity of less than about 13,000 centipoise, and preferably less about 10,000 centipoise.

The term "homogeneously disposed" or "homogeneously dispersed" refers to a mixture in which each of the components are uniformly dispersed within the matrix.

The term "heterogeneously disposed" or "heterogeneously dispersed" refers to a mixture in which the components are not mixed uniformly into a matrix.

The term "solid solution" refers to a homogeneously dispersed mixture of two or more substances. A component that is mixed uniformly in a matrix in such a manner that the component is macroscopically indistinguishable from the matrix itself. An example of a solid solution is a metal alloy, such as brass.

The term "multi-phase mixture" refers to a mixture of two or more substances in which at least one component is macroscopically distinguishable from the matrix itself. An example of a multi-phase mixture is a macro emulsion.

Implantable Medical Devices with Holes

Figure 1:
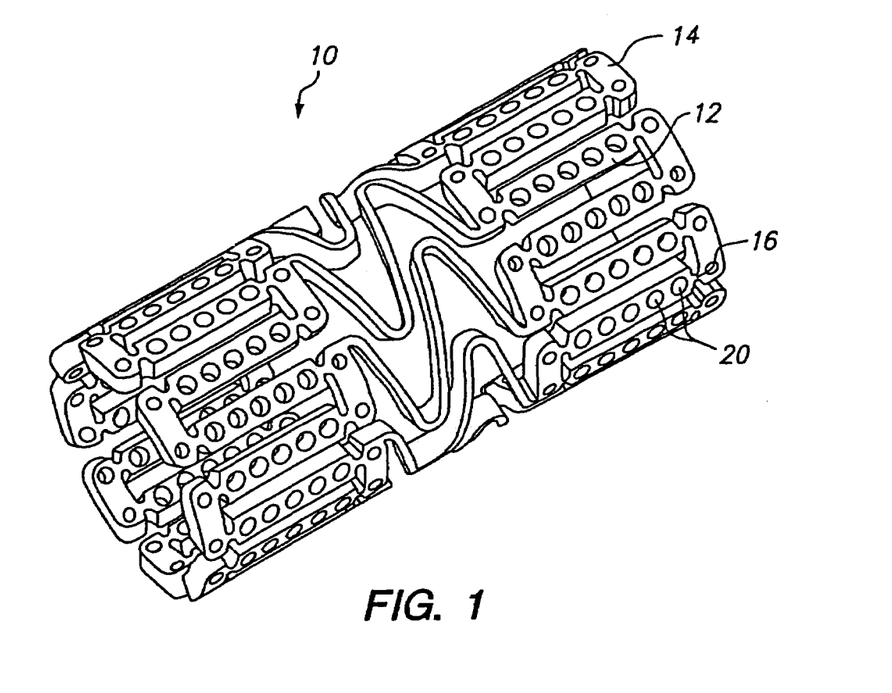
FIG. 1 is a perspective view of a therapeutic agent delivery device in the form of an expandable stent.

FIG. 1 illustrates a medical device 10 according to the present invention in the form of a stent design with large, non-deforming struts 12 and links 14, which can contain holes 20 without compromising the mechanical properties of the struts or links, or the device as a whole. The non-deforming struts 12 and links 14 may be achieved by the use of ductile hinges 16 which are described in detail in U.S. Pat. No. 6,241,762 which is incorporated hereby by reference in its entirety. The holes 20 serve as large, protected reservoirs for delivering various beneficial agents to the device implantation site.

The relatively large, protected openings 20, as described above, make the expandable medical device of the present invention particularly suitable for delivering larger molecules or genetic or cellular agents, such as, for example, protein drugs, enzymes, antibodies, antisense oligonucleotides, ribozymes, gene/vector constructs, and cells (including but not limited to cultures of a patient's own endothelial cells). Many of these types of agents are biodegradable or fragile, have a very short or no shelf life, must be prepared at the time of use, or cannot be pre-loaded into delivery devices such as stents during the manufacture thereof for some other reason. The large holes 20 in the expandable device of the present invention form protected areas or receptors to facilitate the loading of such an agent either at the time of use or prior to use, and to protect the agent from abrasion and extrusion during delivery and implantation.

The volume of beneficial agent that can be delivered using holes 20 is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Holes also decrease the surface area of the beneficial agent bearing compounds to which the vessel wall surface is exposed. For typical devices with beneficial agent openings, this exposure decreases by a factors ranging from about 6:1 to 8:1, by comparison with surface coated stents. This dramatically reduces the exposure of vessel wall tissue to polymer carriers and other agents that can cause inflammation, while simultaneously increasing the quantity of beneficial agent delivered, and improving control of release kinetics.

Figure 2:
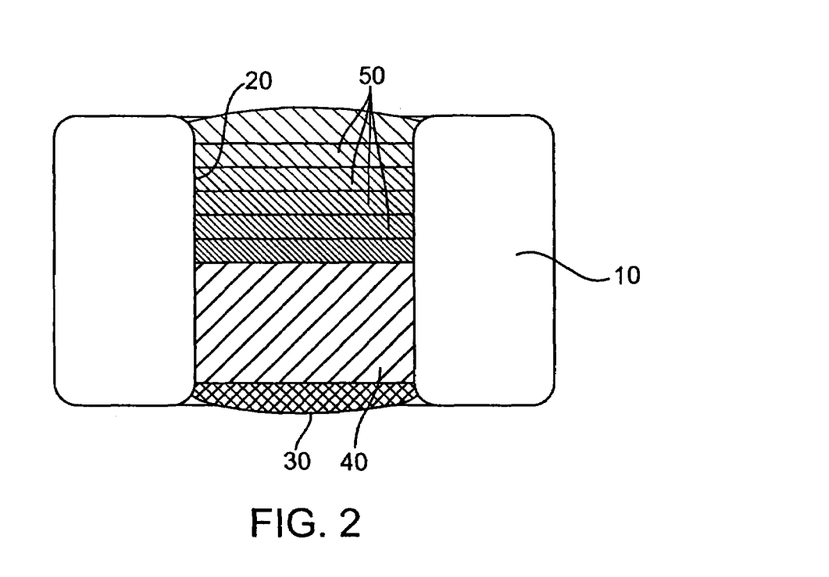
FIG. 2 is a cross sectional view of a portion of a therapeutic agent delivery device having a beneficial agent contained in an opening in layers.

FIG. 2 shows a cross section of a medical device 10 in which one or more beneficial agents have been loaded into the opening 20 in discrete layers 30. Examples of some methods of creating such layers and arrangements of layers are described in U.S. patent application Ser. No. 09/948,989, filed on Sep. 7, 2001, which is incorporated herein by reference in its entirety.

According to one example, the total depth of the opening 20 is about 125 to about 140 microns, and the typical layer thickness would be about 2 to about 50 microns, preferably about 12 microns. Each typical layer is thus individually about twice as thick as the typical coating applied to surface-coated stents. There would be at least two and preferably about ten to twelve such layers in a typical opening, with a total beneficial agent thickness about 4 to 28 times greater than a typical surface coating. According to one preferred embodiment of the present invention, the openings have an area of at least $5\times10^{-6}$ square inches, and preferably at least $7\times10^{-6}$ square inches.

Since each layer is created independently, individual chemical compositions and pharmacokinetic properties can be imparted to each layer. Numerous useful arrangements of such layers can be formed, some of which will be described below. Each of the layers may include one or more agents in the same or different proportions from layer to layer. The layers may be solid, porous, or filled with other drugs or excipients.

FIG. 2 shows an arrangement of layers provided in a through opening 20 which include a barrier layer 30, one or more therapeutic agent layers 40, a plurality of mixing layers 50, and an optional cap layer 60. The barrier layer 30 substantially prevents delivery of the therapeutic agent in the therapeutic agent layers and the mixing layers from being delivered to a side of the device 10 adjacent the barrier layer. The therapeutic agent layer 40 and the mixing layers 50 are loaded sequentially into the medical device opening 20, such that a concentration gradient of therapeutic agent is present with a highest concentration of therapeutic agent at the interior layers closer to the barrier layer and a lowest concentration of therapeutic agent at the exterior mixing layers. The combination of therapeutic agent layer and mixing agent layers allows a water soluble therapeutic agent to be delivered over an extended time period of time. The time period for delivery can be modulated from minutes, to hours, to days. Preferably the time period for delivery is greater than 1 day, more preferably greater than 3 days. The cap layer 60 can be provided at a tissue contacting surface of the device. The cap layer 60 blocks or retards biodegradation of subsequent layers and/or blocks or retards diffusion of the beneficial agent in that direction for a period of time which allows the delivery of the medical device to a desired location in the body. The material of the cap layer can be the same or different from that of the barrier layer.

In one embodiment the layers are loaded into the medical device by first loading the therapeutic agent layer, 40, into the holes of the medical device in a liquefied state. The therapeutic agent layer is then allowed to solidify. A first mixing layer, 50, is then loaded into the holes within the medical device in a liquefied state. When the liquid mixing layer, 50, comes into contact with the therapeutic agent layer, 40, a portion of the therapeutic agent layer is liquefied allowing a co-mingling of some of the components of each of the two layers. When the mixing layer solidifies, there is therapeutic agent within the mixing layer.

Optionally, a second mixing layer is then loaded into the holes within the medical device in a liquefied state. When the second liquid mixing layer comes into contact with the first mixing layer, a portion of the first mixing layer is liquefied allowing a co-mingling of some of the components of each of the two layers. When the mixing layer solidifies, there is an amount of therapeutic agent within the second mixing layer that is less than the amount of therapeutic agent in the first mixing layer. Subsequent additions of mixing layers results in the formation of multiple mixing layers with decreasing amounts of therapeutic agent. The gradient of therapeutic agent incorporated in a mixing layers adjacent the therapeutic agent layer is especially advantageous for the delivery of water soluble drugs such as a 2-chlorodeoxyadenosine.

An example of a binding agent is Poly vinylpyrrolidone. The polymers of the therapeutic agent layer may be the same as or different from the polymer of the mixing layers. The polymer can be liquefied by maintaining the material at a temperature that is greater than its melting point, or glass transition temperature, or by dissolution in a solvent.

Some examples of hydrophobic, bioresorbable matrix materials for the mixing layer are lipids, fatty acid esters, such as glycerides. The erosion rate is controlled by varying the hydrophilic-lipophilic balance (HLB). The polymers of the individual mixing layers may be the same or different. These polymers can be liquefied by maintaining the material at a temperature that is greater than its melting point, or glass transition temperature, or by dissolution in a solvent.

Bioerosion of the mixing layers may induce the release of the therapeutic agent from either the mixing layer or the therapeutic agent layer. However, in some embodiments, the mixing layer remains essentially intact, and the therapeutic agent is released into the reaction environment by diffusing from the therapeutic agent layer and through the mixing layers.

Therapeutic Layer Formulations

The therapeutic agent layers of the present invention may consist of the therapeutic agent alone or a therapeutic agent in combination with a bioresorbable matrix. The matrix of the therapeutic agent layers can be made from pharmaceutically acceptable polymers, such as those typically used in medical devices. This polymer may also be referred to as a binding agent. Typically, when a lesser amount of matrix material is used relative to the amount of drug, for example 5-50% polymer to 95-50% drug, the material is called a binding agent.

Polymers useful in the therapeutic agent layer as either a matrix material or a binding agent are well known and include but are not limited to poly-α-hydroxy acid esters such as, polylactic acid, polyglycolic acid, polylactic-co-glycolic acid, polylactic acid-co-caprolactone; polyethylene glycol and polyethylene oxide; polyvinyl alcohol, polyvinyl pyrrolidone; polyorthoesters; polysaccharides and polysaccharide derivatives such as polyhyaluronic acid, a glycosaminoglycan, polyalginic acid, chitin, chitosan, chitosan derivatives, cellulose, hydroxyethylcellulose, hydroxypropylcellulose, carboxymethylcellulose; polypeptides, and proteins such as polylysine, polyglutamic acid, albumin; polyanhydrides; polyhydroxy alkonoates such as polyhydroxy valerate, polyhydroxy butyrate, and the like, and copolymers thereof. Particularly useful polymers include poly ethylene glycol, poly ethylene oxide, poly vinylpyrrolidone, poly vinyl alcohol, polysaccharides and their derivatives, poly hyaluronic acid, poly alginic acid, chitin, chitosan, chitosan derivatives, cellulose, hydroxyethyl cellulose, hydroxypropyl cellulose, carboxymethyl cellulose, poly peptides, poly lysine, poly glutamic acid, and proteins. These polymers and copolymers can be prepared by methods well known in the art (see, for example, Rempp and Merril: Polymer Synthesis, 1998, John Wiley and Sons) in or can be used as purchased from Alkermes, in Cambridge, Mass. or Birmingham Polymer Inc., in Birmingham, Ala.

The preferred polymer for use in the therapeutic layer of the present invention is poly vinylpyrrolidone (PVP). The rate at which the polymer resorbs is determined by the selection of the subsequently loaded mixing layers.

Therapeutic Agent Formulations

Some drugs that are useful in the present invention are low molecular weight synthetic oligonucleotides and polypeptides, such as 2-chlorodeoxyadenosine, restinase, or restin NG.

Typical formulations for therapeutic agents incorporated in these medical devices are well known to those skilled in the art and include but are not limited to solid particle dispersions, encapsulated agent dispersions, and emulsions, suspensions, liposomes or microparticles, wherein said liposome or microparticle comprise a homogeneous or heterogeneous mixture of the therapeutic agent.

The amount of the drug that is present in the device, and that is required to achieve a therapeutic effect, depends on many factors, such as the minimum necessary dosage of the particular drug, the condition to be treated, the chosen location of the inserted device, the actual compound administered, the age, weight, and response of the individual patient, the severity of the patient's symptoms, and the like.

The appropriate dosage level of the therapeutic agent, for more traditional routes of administration, are known to one skilled in the art. These conventional dosage levels correspond to the upper range of dosage levels for compositions, including a physiologically active substance and traditional penetration enhancer. However, because the delivery of the active substance occurs at the site where the drug is required, dosage levels significantly lower than a conventional dosage level may be used with success. Ultimately, the percentage of therapeutic agent in the composition is determined by the required effective dosage, the therapeutic activity of the particular formulation, and the desired release profile. In general, the active substance will be present in the composition in an amount from about 0.0001% to about 99%, more preferably about 0.01% to about 80% by weight of the total composition depending upon the particular substance employed. However, generally the amount will range from about 0.05% to about 75% by weight of the total composition.

Mixing Layer Formulations

The mixing layers of the present invention are comprised of a bioresorbable matrix and optionally contain additional additives, therapeutic agents, activating agents, deactivating agents, and the like as described in U.S. patent application Ser. No. 10/253,020. In addition to the polymer materials described above, the mixing layer may also be comprised of pharmaceutically acceptable lipids or lipid derivatives, which are well known in the art and include but are not limited to fatty acids, fatty acid esters, lysolipids, phosphocholines, (Avanti Polar Lipids, Alabaster, Ala.), including 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine; dimyristoyl-phosphatidylcholine; dipentadecanoylphosphatidylcholine; dilauroylphosphatidyl-choline; dipalmitoylphosphatidylcholine (DPPC); distearoylphosphatidylcholine (DSPC); and diarachidonyiphosphatidyicholine (DAPC); phosphatidyl-ethanolamines, such as dioleoylphosphatidylethanolamine, dipahnitoyl-phosphatidylethanolamine (DPPE) and distearoylphosphatidylefhanolamine (DSPE); phosphatidylserine; phosphatidylglycerols, including distearoylphosphatidylglycerol (DSPG); phosphatidylinositol; sphingolipids such as sphingomyelin; glucolipids; sulfatides; glycosphingolipids; phosphatidic acids, such as dipahmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids", with preferred lipids bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose diacetate hexaisobutyrate (SAIB), sucrose laurate, fructose laurate, sucrose palritate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol monolaurate, glycerol dipalmitate, glycerol and glycerol esters including glycerol tripalmitate, glycerol monopalmitate, glycerol distearate, glycerol tristearate, glycerol monostearate, glycerol monomyristate, glycerol dimyristate, glycerol trimyristate; long chain alcohols including n-decyl alcohol, lauryl alcohol, myristyl alcohol, cetyl alcohol, and n-octadecyl alcohol; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

These lipid materials are well known in the art and can be used as purchased from Avanti, Burnaby, B.C. Canada.

The preferred lipids for use in the present invention are phosphatidyl-choline, phosphatidylethanolamine, phosphatidylserine, sphingomyelin as well as synthetic phospholipids such as dimyristoyl phosphatidylcholine, dipalmitoyl phosphatidylcholine, distearoyl phosphatidylcholine, distearoyl phosphatidyl-glycerol, dipalmitoyl phosphatidylglycerol, dimyristoyl phosphatidylserine, distearoyl phosphatidylserine and dipalmitoyl phosphatidylserine.

The rate at which the bioresorbable matrix resorbs is determined by the choice of lipid, the molecular weight, and the ratio of the chosen materials.

The mixing layer can resorb by either chemical mechanisms such as chemical interactions, dissolution in water, hydrolysis, or reaction with enzymes, or by physical erosion mechanisms.

Composite Matrix of Therapeutic Agent and Mixing Layers

Because of the methods used to make the implantable devices of the present invention, the therapeutic agent that is first incorporated in the therapeutic agent layer is ultimately found throughout the therapeutic agent layer and the mixing layers. Each layer is introduced into the holes of the device while in a liquified state and then is allowed to solidify. A layer previously solidified within the wells is partially liquefied again when a new liquified layer is introduced on top of the existing solid layer. This allows for the materials of these two layers to mix. The concentration of a therapeutic agent in a later applied layer is going to be smaller than the concentration of therapeutic agent in the previously formed layers. This layer method allows for a concentration gradient of therapeutic agent to be formed in the layers within the medical device.

The mixing layer and the therapeutic agent layer, into which the therapeutic agent is homogeneously or heterogeneously dispersed, may each be a homogeneous or heterogeneous mixture. For example, if the polymers of the mixing layer and the polymers of the therapeutic agent layer are mutually miscible, then the material contained within the holes of the implantable medical device will be a solid solution, or a one phase mixture, comprising each of these polymers. Examples of polymer systems that can form a one phase homogeneous mixture include but are not limited to 1) polyvinyl pyrrolidone and poly vinyl alcohol, 2) polyvinyl pyrrolidone and polyethylene glycol, 3) polyvinyl pyrrolidone and polyalginate, and 4) polyvinyl pyrrolidone and carboxymethylcellulose.

If the polymers comprising the mixing layer and therapeutic agent layer are only slightly miscible or are immiscible, then the material contained within the holes of the implantable medical device will be a two phase -(or phase separated) mixture comprising each of these polymers. The two phase mixture may be i) phase domains of the mixing layer polymer dispersed in a continuous phase of the therapeutic agent layer polymer;

ii) phase domains of the therapeutic agent layer polymer dispersed in a continuous phase of the mixing layer polymer; or iii) two co-continuous phases each of the mixing layer polymer and the therapeutic agent layer polymer.

The type of two-phase mixture is determined by judicious choice of polymer for each layer, and the percentage of each polymer that dissolves in the solvent used to introduce the mixing layer(s). Examples of polymer systems that can form a multi-phase homogeneous mixture include but are not limited to 1) 50% by volume of polylactide and 50% by volume of poly vinylpyrrolidone 2) Poly(lactide-co-glycolide) and polyethylene oxide, and 3) poly DL-lactide and polyethylene oxide.

Additionally, two phase mixtures can be prepared such that one phase is a homogeneous mixture of a first weight ratio of mixing layer polymer and therapeutic agent layer polymer and a second phase is a is a homogeneous mixture of a second weight ratio of the same mixing layer polymer and therapeutic agent layer polymer. Generally, to achieve phase separation and a resulting two phase mixture, one phase will consist largely of mixing layer polymer and a second phase will consist largely of therapeutic agent layer polymer.

The therapeutic agent maybe homogeneously or heterogeneously disposed within the homogeneous or heterogeneous matrix formed by the polymers of the mixing layer and the therapeutic agent layer. For example, if the therapeutic agent is fully soluble in each of the mixing layer and therapeutic agent layer polymers, then the distribution of the therapeutic agent will be controlled by the relative solubility of the agent in each polymer and the relative miscibility of the polymers in each other as well as their respective volume proportions. If the desired amount of therapeutic agent exceeds the solubility in either or both of the mixing layer or the therapeutic agent layer, then the therapeutic agent can theoretically be found in four separate phases within the final composite matrix.

1) homogeneously dissolved in the mixing layer polymer;

2) dispersed as a second phase within the mixing layer polymer;

3) homogeneously dissolved in the therapeutic agent layer polymer which is itself in a continuous or non-continuous phase with respect to the therapeutic agent layer; or 4) dispersed as a second phase within the therapeutic agent layer polymer.

The distribution of the therapeutic agent, and thus the kinetic release profile, may be controlled by the selection of the molecular weight of the polymer, the solubility of the polymer and the volume percentage of each of the polymers used within the mixing and the therapeutic agent layers.

Any of the specific polymers or chemicals listed as a useful matrix material for the mixing layer may also be used in the therapeutic agent layer as a binder and vise-versa. Generally, the material chosen as a binding agent in therapeutic agent layer has different physical properties than the material used as the matrix in the mixing layers. This may be accomplished by using two different chemicals or polymers. Alternatively, the same type of polymer maybe used as long as the physical properties, such as solubility, or hydrophobicity, hydrophilicity or melting point or glass transition temperature can be altered by changing the polymers molecular weight or by adding additional components or additives, such as co-polymers, elasticizers, plasticizers and the like.

The therapeutic agent, which can be heterogeneously or homogeneously dispersed in the therapeutic agent layer and/or the mixing layer, can be a drug, or a drug formulated into a microcapsule, niosome, liposome, microbubble, microsphere, or the like. In addition, the mixing layer may contain more than one therapeutic agent. For example, a water sensitive drugs, such as a limus, or any other drug that must be administered through intravenous, intramuscular, or subcutaneously, could be incorporated in a hydrophobic matrix such as SAIB, or fatty acid ester.

Bioresorbable polymers may also be used to form barrier layers that resorb at a rate that can be predetermined base on the composition and that contain no therapeutic agent.

In one embodiment, the mixing layers, 50, of the present invention are essentially hydrophobic and are bioresorbed at a rate that can be selected based on the polymers that are chosen in the formulation. The therapeutic agent layer, 40, is comprised of about 50% to about 60% of a therapeutic agent and about 40% to about 50% of a pharmaceutically acceptable bioresorbable polymer that acts primarily as a binding agent.

Uses for Implantable Medical Devices

Although the present invention has been describe with reference to a medical device in the form of a stent, the medical devices of the present invention can also be medical devices of other shapes useful for site-specific and time-release delivery of drugs to the body and other organs and tissues. The drugs may be delivered to the vasculature including the coronary and peripheral vessels for a variety of therapies, and to other lumens in the body including the esophagus, urethera, and the bile duct. The drugs may increase lumen diameter, create occlusions, or deliver the drug for other reasons.

Medical devices and stents, as described herein, are useful for the prevention of amelioration of restenosis, particularly after percutaneous transluminal coronary angioplasty and intraluminal stent placement. In addition to the timed or sustained release of anti-restenosis agents, other agents such as anti-inflammatory agents may be incorporated in to the multi-layers incorporated in the plurality of holes within the device. This allows for site-specific treatment or prevention any complications routinely associated with stent placement that are known to occur at very specific times after the placement occurs.

The methods for loading beneficial agents into openings in an expandable medical device may include known techniques such as dipping and coating and also known piezoelectric micro-jetting techniques. Micro-injection devices may be used to deliver precise amounts of one or more liquid beneficial agents including mixing layers, therapeutic agent layers, and any other layers to precise locations on the expandable medical device in a known manner. The beneficial agents may also be loaded by manual injection devices.

EXAMPLES

In the examples below, the following abbreviations have the following meanings. If an abbreviation is not defined, it has its generally accepted meaning.

mL=milliliters
M=Molar
wt.=weight
vol.=volume
μL=microliters
μm=micrometers
nm=nanometers
DMSO=Dimethyl sulfoxide
NMP=N-methylpyrrolidone
DMAC=Dimethyl acetamide

Example 1

Formulation Comprising a Gradient of a Therapeutic Agent Within the Mixing Layers A first mixture of poly(lactide-co-glycolide) (PLGA) (Birmingham Polymers, Inc), lactide:glycolide::85:15, ($M_v$>100,000 Daltons) 7% wt. and a suitable organic solvent, such as DMSO, NMP, or DMAC 93% wt. is prepared. The mixture is loaded dropwise into holes in the stent, then the solvent is evaporated to begin formation of the barrier layer. A second barrier layer is laid over the first by the same method of filling polymer solution into the hole followed by solvent evaporation. The process is continued until five individual layers have been laid down to form the barrier layer.

A second mixture of 2-chlorodeoxyadenosine, 50% solids basis, and poly vinylpyrrolidone (PVP), 50% solids basis, in a suitable organic solvent, such as DMSO, is introduced into holes in the stent over the barrier layer. The solvent is evaporated to form a drug filled therapeutic agent layer. The filling and evaporation procedure is repeated until the hole is filled to about 50% of its total volume with drug in therapeutic agent layer layered on top of the barrier layer.

Three layers of a third solution, of poly(lactide-co-glycolide) (PLGA), lactide:glycolide::50:50, ($M_v$≅80,000 Daltons) 8% wt. and a suitable organic solvent, such as DMSO, are then laid down over the therapeutic agent layer to form three mixing layers. When each of the mixing layers is loaded into the stent, a portion of the layer beneath is incorporated in the new layer. In this way multiple mixing layers are formed containing a concentration gradient of therapeutic agent.

Following implantation of the filled stent in vivo, the 2-chlorodeoxyadenosine contained within the stent is delivered slowly over a time period of about 1 to about 8 days. The barrier layer prevents the therapeutic agent from being delivered out the barrier layer side of holes in the stent.

Example 2

Measurement of Drug Release Rates from a Medical Device with Multiple Therapeutic Agent Layers A solution of phosphate buffered saline (PBS) is prepared by dissolving five "Phosphate Buffered Saline Tablets" (Sigma-Aldrich Co., catalog #P-4417) in 1000 mL deionized water to provide a solution with a pH of 7.4, 0.01 M in phosphate buffer, 0.0027 M in potassium chloride and 0.137 M in sodium chloride. This PBS solution is used as a Release Solution.

The elution rate of drug from the multilayered stent of Example 1 is determined in a standard sink condition experiment.

A first 10 mL screw capped vial is charged with release solution, 3 mL, then placed in a shaking water bath held at 37° C. until temperature has equilibrated. The above stent containing a concentration gradient of drug in the mixing layers is placed into the release solution, shaking at 60 cycles per minute commenced, and the stent is held immersed in the release solution for a period of time. The stent is then placed in a second screw capped vial is charged with release solution, 3 mL, at 37° C., and held for a period of time. The first release solution is called sample #1. From time to time, the stent is removed from release solution in one vial and placed into fresh solution in the next vial to generate a series of samples containing varying amounts of drug eluted from the stent.

The amount of drug in a given release solution sample is determined by High Pressure Liquid Chromatography (HPLC). The following conditions are used:

Analysis Column: Sym. $C_{18}$ (5 μm, 3.9×150 mm, Waters Corp., Mass.)
Mobile phase: Water/Acetonitrile:: 55% vol./45% vol.
Flow Rate: 1 mL/minute
Temperature: 25° C.
Detection wavelength: 227 nm
Injection volume: 50 μL
Retention time: 10.5 minutes By comparison with a calibration curve generated from known stock solutions, the amount of drug eluted into the release solution during any time period of the experiment can be calculated.

Methods and results for measuring release profiles are published in A. Finkelstein et al., "The Conor Medsystems Stent: A programmable Drug Delivery Device," TCT 2001 Conference, Washington, D.C., September 2001.

While the invention has been described in detail with reference to the preferred embodiments thereof, it will be apparent to one skilled in the art that various changes and modifications can be made and equivalents employed, without departing from the present invention.

What is claimed is:

1. An implantable medical device comprising:
   an implantable device body having a plurality of holes;
   a therapeutic agent provided in a first therapeutic agent layer and contained within the plurality of holes in the device body; and
   at least one mixing layer provided adjacent the first therapeutic agent layer in the plurality of holes;
   wherein the therapeutic agent layer and the at least one mixing layer together contain a continuous concentration gradient of said therapeutic agent and allow for the controlled release of the therapeutic agent contained within the therapeutic agent layer and the at least one mixing layer.

2. The implantable medical device of claim 1, wherein the at least one mixing layer is a pharmaceutically acceptable bioresorbable matrix that allows the therapeutic agent contained within the therapeutic agent layer and the at least one mixing layer to be released as the matrix resorbs.

3. The implantable medical device of claim 2, wherein said pharmaceutically acceptable bioresorbable matrix comprises at least one pharmaceutically acceptable polymer.

4. The implantable medical device of claim 3, wherein said pharmaceutically acceptable polymer is selected from the group consisting of polylactic acid, polyglycolic acid, polylactic-co-glycolic acid, polylactic acid-co-caprolactone, polyethylene glycol, polyethylene oxide, poly lactic acid-block-poly ethylene glycol, poly glycolic acid-block-poly ethylene glycol, poly lactide-co-glycolide-block-poly ethylene glycol, poly ethylene glycol-block-lipid, polyvinyl pyrrolidone, poly vinyl alcohol, a glycosaminoglycan, polyorthoesters, polysaccharides, polysaccharide derivatives, polyhyaluronic acid, polyalginic acid, chitin, chitosan, chitosan derivatives, cellulose, hydroxyethylcellulose, hydroxypropylcellulose, carboxymethylcellulose, polypeptides, polylysine, polyglutamic acid, albumin, polyanhydrides, polyhydroxy alkonoates, polyhydroxy valerate, polyhydroxy butyrate, proteins, polyphosphate esters, lipids, and mixtures thereof.

5. The implantable medical device of claim 4, wherein said therapeutic agent from the therapeutic agent layer is homogeneously dispersed as a solid solution in said at least one mixing layer.

6. The implantable medical device of claim 4, wherein said therapeutic agent is homogeneously dispersed as multi-phase mixture in said at least one mixing layer.

7. The implantable medical device of claim 4, wherein said therapeutic agent from the therapeutic agent layer is heterogeneously disposed in said at least one mixing layer.

8. The implantable medical device of claim 7, wherein said therapeutic agent from the therapeutic agent layer is homogeneously or heterogeneously disposed in said at least one mixing layer as a solid particle dispersion, encapsulated agent dispersion, an emulsion, a suspension, a liposome, niosome, or a microparticle, wherein said niosome, liposome or microparticle comprise a homogeneous or heterogeneous mixture of the therapeutic agent.

9. The implantable medical device of claim 1, wherein the therapeutic agent layer comprises the therapeutic agent and a water soluble binding agent.

10. The implantable medical device of claim 9, wherein the binding agent is a pharmaceutically acceptable polymer selected from the group consisting of poly ethylene glycol, poly ethylene oxide, poly vinylpyrrolidone, poly vinyl alcohol, a glycosaminoglycan, polysaccharides, polysaccharide derivatives, poly hyaluronic acid, poly alginic acid, chitin, chitosan, chitosan derivatives, cellulose, hydroxyethyl cellulose, hydroxypropyl cellulose, carboxymethyl cellulose, poly peptides, poly lysine, poly glutamic acid, and proteins.

11. The implantable medical device of claim 9, wherein the at least one mixing layer includes a polymer different from the water soluble binding agent 12. The implantable medical device of claim 11, wherein the at least one mixing layer includes a plurality of mixing layers formed by a process comprising:
   sequentially delivering a substantially identical composition to the implantable medical device for each of the layers which take on the concentration gradient into the plurality of holes.

13. The implantable medical device of claim 1, wherein the at least one mixing layer is formed by a process comprising:
   delivering a polymer without the therapeutic agent to the holes; and
   liquefying a portion of the therapeutic agent layer with said polymer, the at least one mixing layer acquiring therapeutic agent from the therapeutic agent layer.

14. The implantable medical device of claim 9, wherein said therapeutic agent is homogeneously dispersed as a solid solution in said therapeutic agent layer.

15. The implantable medical device of claim 9, wherein said therapeutic agent is homogeneously dispersed as multiphase mixture in said therapeutic agent layer.

16. The implantable medical device of claim 9, wherein said therapeutic agent is heterogeneously disposed in said therapeutic agent layer.

17. The implantable medical device of claim 9, wherein said therapeutic agent is homogeneously or heterogeneously disposed in said therapeutic agent layer as a solid particle dispersion, encapsulated agent dispersion, an emulsion, a suspension, a liposome, niosome, or a microparticle, wherein said niosome, liposome or microparticle comprise a homogeneous or heterogeneous mixture of the therapeutic agent.

18. The implantable medical device of claim 1, wherein the therapeutic agent is selected from the group consisting of antithrombotic agents, antineoplastic agents, neoplastic agents, antiproliferative agents, antisense compounds, immunosuppresants, angiogenic agents, angiogenic factors, anti-angiogenic agents, and anti-inflammatory agents, or combinations thereof.

19. The implantable medical device of claim 1, wherein the therapeutic agent is selected from the group consisting of 2-chlorodeoxyadenosine, bivalirudin, Resten NG, and an oliogonucleotide.

20. The implantable medical device of claim 1, wherein said therapeutic agent is an agent selected for treatment of restenosis or inflammation.

21. The implantable medical device of claim 1, wherein the implantable medical device is a stent.

22. An implantable medical device comprising:
   an implantable device body having a plurality of holes;
   a therapeutic agent within the plurality of holes in the device body provided in a therapeutic agent layer; and
   a mixing layer provided in the plurality of holes;
   wherein the therapeutic agent layer and the mixing layer contain a continuous concentration gradient of said therapeutic agent created by a process comprising
      delivering a mixing layer material without the therapeutic agent, and liquefying a portion of the therapeutic agent layer with the mixing layer material, wherein the mixing layer has a smaller amount of therapeutic agent contained therein than the therapeutic agent layer.

23. The implantable medical device of claim 22, wherein the mixing layer is a pharmaceutically acceptable bioresorbable matrix that allows the therapeutic agent contained within the therapeutic agent layer and the mixing layer to be released as the matrix resorbs.

24. The implantable medical device of claim 23, wherein said bioresorbable matrix comprises at least one pharmaceutically acceptable polymer.

25. The implantable medical device of claim 24, wherein said pharmaceutically acceptable polymer is selected from the group consisting of polylactic acid, polyglycolic acid, polylactic-co-glycolic acid, polylactic acid-co-caprolactone, polyethylene glycol, polyethylene oxide, poly lactic acid-block-poly ethylene glycol, poly glycolic acid-block-poly ethylene glycol, poly lactide-co-glycolide-block-poly ethylene glycol, poly ethylene glycol-block-lipid, polyvinyl pyrrolidone, poly vinyl alcohol, a glycosaminoglycan, polyorthoesters, polysaccharides, polysaccharide derivatives, polyhyaluronic acid, polyalginic acid, chitin, chitosan, chitosan derivatives, cellulose, hydroxyethylcellulose, hydroxypropylcellulose, carboxymethylcellulose, polypeptides, polylysine, polyglutamic acid, albumin, polyanhydrides, polyhydroxy alkonoates, polyhydroxy valerate, polyhydroxy butyrate, proteins, polyphosphate esters, lipids, and mixtures thereof.

26. The implantable medical device of claim 24, wherein the therapeutic agent layer comprises at least one pharmaceutically acceptable polymer different from the pharmaceutically acceptable polymer of the mixing layer.

27. The implantable medical device of claim 22, wherein the therapeutic agent layer comprises the therapeutic agent and a water soluble binding agent.

28. The implantable medical device of claim 27, wherein the binding agent is a pharmaceutically acceptable polymer selected from the group consisting of poly ethylene glycol, poly ethylene oxide, poly vinylpyrrolidone, poly vinyl alcohol, a glycosaminoglycan, polysaccharides, polysaccharide derivatives, poly hyaluronic acid, poly alginic acid, chitin, chitosan, chitosan derivatives, cellulose, hydroxyethyl cellulose, hydroxypropyl cellulose, carboxymethyl cellulose, poly peptides, poly lysine, poly glutamic acid, and proteins.

29. The implantable medical device of claim 27, wherein said therapeutic agent is homogeneously dispersed as a solid solution in said therapeutic agent layer.

30. The implantable medical device of claim 27, wherein said therapeutic agent is homogeneously dispersed as multiphase mixture in said therapeutic agent layer.

31. The implantable medical device of claim 27, wherein said therapeutic agent is heterogeneously disposed in said therapeutic agent layer.

32. The implantable medical device of claim 31, wherein said therapeutic agent is homogeneously or heterogeneously disposed in said therapeutic agent layer as a solid particle dispersion, encapsulated agent dispersion, an emulsion, a suspension, a liposome, niosome, or a microparticle, wherein said niosome, liposome or microparticle comprise a homogeneous or heterogeneous mixture of the therapeutic agent.

33. The implantable medical device of claim 27, wherein said therapeutic agent from the therapeutic agent layer is homogeneously dispersed as a solid solution in said mixing layer.

34. The implantable medical device of claim 27, wherein said therapeutic agent from the therapeutic agent layer is homogeneously dispersed as multi-phase mixture in said mixing layer.

35. The implantable medical device of claim 27, wherein said therapeutic agent from the therapeutic agent layer is heterogeneously disposed in said mixing layer.

36. The implantable medical device of claim 35, wherein said therapeutic agent from the therapeutic agent layer is homogeneously or heterogeneously disposed in said mixing layer as a solid particle dispersion, encapsulated agent dispersion, an emulsion, a suspension, a liposome, niosome, or a microparticle, wherein said niosome, liposome or microparticle comprise a homogeneous or heterogeneous mixture of the therapeutic agent.

37. The implantable medical device of claim 22, wherein the therapeutic agent is selected from the group consisting of antithrombotic agents, antineoplastic agents, neoplastic agents, antiproliferative agents, antisense compounds, immunosuppresants, angiogenic agents, angiogenic factors, anti-angiogenic agents, and anti-inflammatory agents, or combinations thereof.

38. The implantable medical device of claim 22, wherein the therapeutic agent is selected from the group consisting of 2-chlorodeoxyadenosine, bivalirudin, Resten NG, and an oliogonucleotide.

39. The implantable medical device of claim 22, wherein said therapeutic agent is an agent selected for treatment of restenosis or inflammation.

40. The implantable medical device of claim 22, wherein the implantable medical device is a stent.

41. A method for preparing an implantable medical device, which method comprises:
   a) providing an implantable medical device with a plurality of holes;
   b) loading into the plurality of holes an amount of a liquefied therapeutic agent, which amount is sufficient to form a therapeutic agent layer;
   c) allowing said liquefied therapeutic agent layer to at least partially solidify;
   d) loading into the plurality of holes an amount of a liquefied bioresorbable polymer which amount is sufficient to liquefy a portion of the therapeutic agent layer, thereby causing a portion of the therapeutic agent to be disposed within a mixing layer;
   e) allowing said liquefied bioresorbable polymer and said portion of the therapeutic agent layer to solidify;
   wherein an amount of therapeutic agent contained within the mixing layer upon solidification is smaller than an amount of therapeutic agent contained in the therapeutic agent layer; and
   further wherein steps d and e may optionally be repeated to form multiple mixing layers.

42. The method for preparing an implantable medical device of claim 41, comprising:
   liquefying the therapeutic agent by maintaining the therapeutic agent at a temperature that is higher than its melting point, or glass transition temperature.

43. The method for preparing an implantable medical device of claim 41, comprising:
   forming the liquefied therapeutic agent by dissolving the therapeutic agent in a solvent.

44. The method for preparing an implantable medical device of claim 41, comprising:
   liquefying the bioresorbable polymer by maintaining the bioresorbable polymer at a temperature that is higher than its melting point, or glass transition temperature.

45. The method for preparing an implantable medical device of claim 41, comprising:
   forming the liquefied bioresorbable polymer by dissolving the bioresorbable polymer in a solvent.

46. The method for preparing an implantable medical device of claim 41, further comprising:

forming a barrier layer by loading into the plurality of holes an amount of a liquefied biocompatible polymer, which amount is sufficient to form a barrier layer, wherein said loading is performed so that the barrier layer is located adjacent the therapeutic agent layer.

47. The method for preparing an implantable medical device of claim 46, comprising:

liquefying the biocompatible polymer by maintaining the biocompatible polymer at a temperature that is higher than its melting point, or glass transition temperature.

48. The method for preparing an implantable medical device of claim 46, comprising:

forming the liquefied biocompatible polymer by dissolving the biocompatible polymer in a solvent.

49. The method for preparing an implantable medical device of claim 41, wherein loading the liquefied bioresorbable polymer into the holes comprises loading liquefied bioresorbable polymer which does not contain the therapeutic agent.

50. The method for preparing an implantable medical device of claim 41, wherein the liquefied therapeutic agent layer comprises the therapeutic agent and a pharmaceutically acceptable polymer.

51. The method for preparing an implantable medical device of claim 50, wherein the liquefied therapeutic agent layer comprises from about 50% to about 95% therapeutic agent and from about 5% to about 50% pharmaceutically acceptable polymer.

52. The method for preparing an implantable medical device of claim 41, wherein loading of the liquefied therapeutic agent and the liquefied bioresorbable polymer comprises dropwise loading.

53. The method for preparing an implantable medical device of claim 41, wherein loading of the liquefied therapeutic agent and the liquefied bioresorbable polymer comprises loading with a piezoelectric micro-jetting device.

54. An implantable medical device comprising:

an implantable device body having a plurality of through holes;

a plurality of layers of a bioresorbable polymer formed in the through holes to form a barrier layer at a first side of the holes;

a plurality of layers of a bioresorbable polymer and drug formed in the through holes to form a drug layer adjacent the barrier layer;

a plurality of layers of a bioresorbable polymer formed in the through holes to form a cap layer at a second side of the holes; and wherein the drug layer and the cap layer mix to form a continuous concentration gradient.

55. The implantable medical device of claim 54, wherein the drug layer comprises 2-chlorodeosyadenosine.

56. The implantable medical device of claim 54, wherein the drug layer comprises paclitaxel.

57. The implantable medical device of claim 54, wherein the drug layer comprises rapamycin.

58. The implantable medical device of claim 54, wherein the barrier layer bioresorbable polymer and the drug layer bioresorbable polymer are different.

59. The implantable medical device of claim 54, wherein the barrier layer bioresorbable polymer and the cap layer bioresorbable polymer are the same.

* * * * *